(12) United States Patent
Stillson

(10) Patent No.: US 9,987,438 B2
(45) Date of Patent: Jun. 5, 2018

(54) TAMPER EVIDENT LOCK IV NEEDLE CAP

(71) Applicant: Randall Stillson, Whitefish, MT (US)

(72) Inventor: Randall Stillson, Whitefish, MT (US)

( * ) Notice: Subject to any disclaimer, the term of this patent is extended or adjusted under 35 U.S.C. 154(b) by 865 days.

(21) Appl. No.: 14/289,889

(22) Filed: May 29, 2014

(65) Prior Publication Data
US 2014/0364804 A1 Dec. 11, 2014

Related U.S. Application Data

(60) Provisional application No. 61/831,668, filed on Jun. 6, 2013.

(51) Int. Cl.
*A61M 5/50* (2006.01)
*A61M 5/162* (2006.01)
*A61M 5/32* (2006.01)
*A61M 5/34* (2006.01)

(52) U.S. Cl.
CPC ........ *A61M 5/5086* (2013.01); *A61M 5/1626* (2013.01); *A61M 5/3202* (2013.01); *A61M 5/3213* (2013.01); *A61M 5/34* (2013.01); *A61M 5/50* (2013.01)

(58) Field of Classification Search
CPC .............. A61M 5/5086; A61M 5/1626; A61M 5/3202; A61M 5/3213; A61M 2005/3215; A61M 5/34; A61M 5/344; A61M 5/50
See application file for complete search history.

(56) References Cited

U.S. PATENT DOCUMENTS

| 4,286,640 | A |   | 9/1981 | Knox et al. |   |
|---|---|---|---|---|---|
| 4,372,593 | A | * | 2/1983 | Kesselman | ........... F16B 41/005 292/307 B |
| 5,531,695 | A |   | 7/1996 | Swisher |   |
| 7,678,101 | B2 |   | 3/2010 | Sage |   |
| 8,091,727 | B2 |   | 1/2012 | Domkowski |   |
| 2004/0054334 | A1 | * | 3/2004 | Prais | ..................... A61B 17/205 604/263 |
| 2005/0101932 | A1 | * | 5/2005 | Cote | ..................... A61M 5/158 604/506 |
| 2007/0185441 | A1 | * | 8/2007 | Fangrow, Jr. | ......... A61M 5/158 604/93.01 |
| 2009/0179422 | A1 | * | 7/2009 | Werth | ................. F16L 33/2071 285/243 |

* cited by examiner

*Primary Examiner* — Bradley J Osinski
*Assistant Examiner* — Nilay Shah
(74) *Attorney, Agent, or Firm* — Harpman & Harpman

(57) ABSTRACT

A tamper resistant/evident cap cover for IV needle configurations to provide a single use engageable cap to prevent unauthorized access and use of an IV needle port. The cap cover has a threaded IV needle receiving base and a slidably disposed interengagement locking clasp. Oppositely disposed tamper evident latching tabs are receivably secured into the base by multiple clasp barbs defining a first position for access and a second closed locked position.

3 Claims, 4 Drawing Sheets

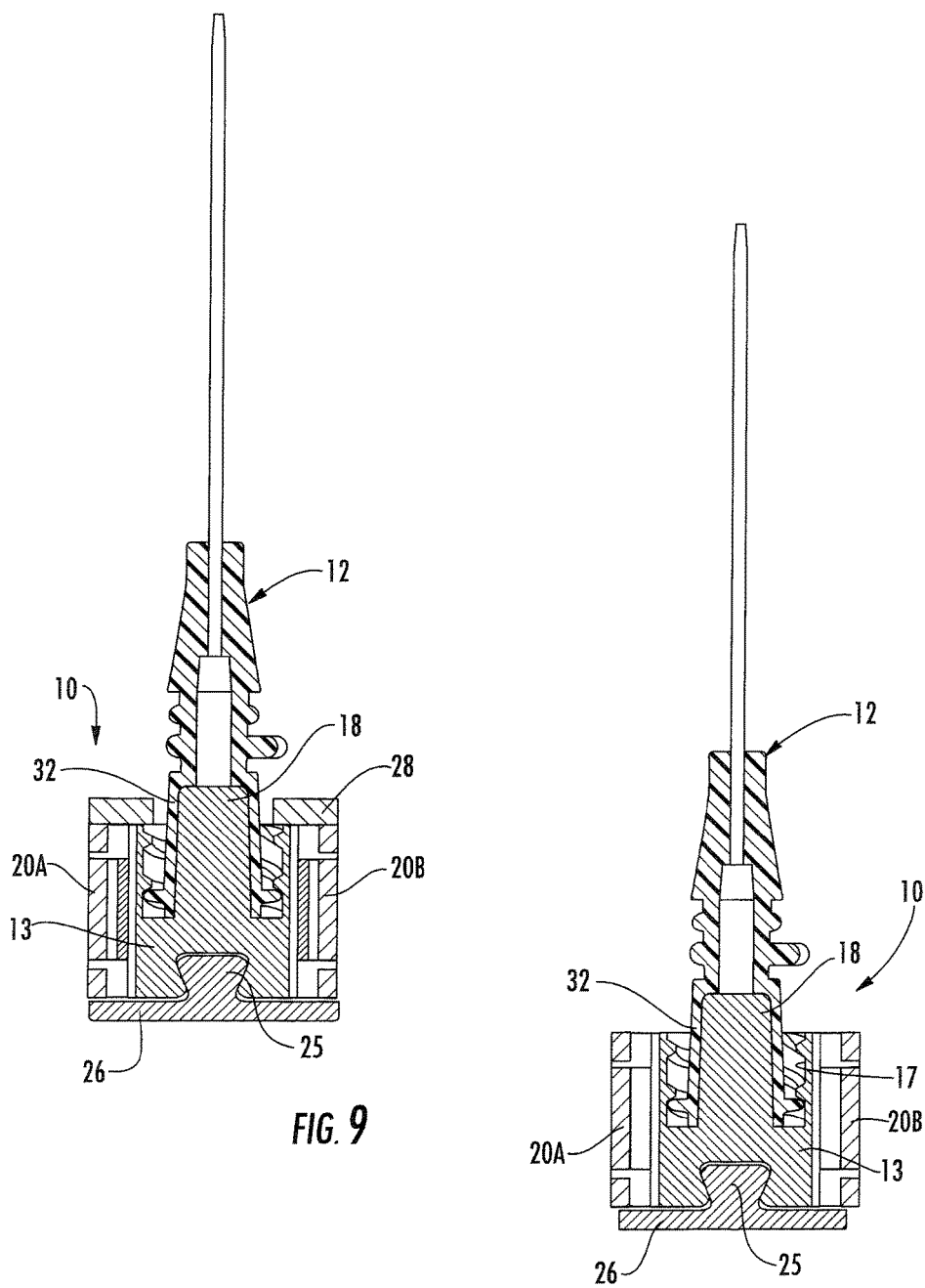

TAMPER EVIDENT LOCK IV NEEDLE CAP

This application claims the benefit of U.S. Provisional Application No. 61/831,668, filed Jun. 6, 2013.

BACKGROUND OF THE INVENTION

1. Technical Field

This invention relates to tamper resistant and evident covers for medical equipment, specifically IV needle assemblies used universally throughout the medical equipment industry.

2. Description of Prior Art

Prior art devices of this type have relied on a variety of different closure strategies, see for example U.S. Pat. Nos. 4,286,640, 5,513,695, 7,678,101 and 8,091,727.

In U.S. Pat. No. 4,286,640 a hinged tamper proof cover can be seen having a pair of hemispherical body members hinged together along adjacent sidewall edges.

U.S. Pat. No. 5,513,695 illustrates a tamper evident sleeve for IV needles that have a pair of elongated hinge covers with a hinge which is removable to access a needle by user engagement pull tab extending therefrom.

U.S. Pat. No. 7,678,101 is directed to a locking catheter connector and connector system.

Finally, in U.S. Pat. No. 8,091,727 a snap over clam shell protective port cap is claimed having two halves hinged together with a puncture resistant lid portion so as to cover when applied onto the end of an injection port.

SUMMARY OF THE INVENTION

A tamper resistant and evident IV needle cover for receiving and securing the access portion of an IV needle configuration to prevent unauthorized IV needle use without direct evidence of such use. An integrated two part cover assembly has a needle threaded receiving and stabilization base with a trans-axially aligned and engageable closure clasp with dual spaced opposing registerable locking tabs defining a first needle insert open position and a second needle engagement clasp closed locking position therebetween.

DESCRIPTION OF THE DRAWINGS

FIG. 9 is a cross sectional view on lines 9-9 of FIG. 4.

FIG. 10 is a cross sectional view on lines 10-10 of FIG. 3.

DETAILED DESCRIPTION OF THE INVENTION

Figure 1:
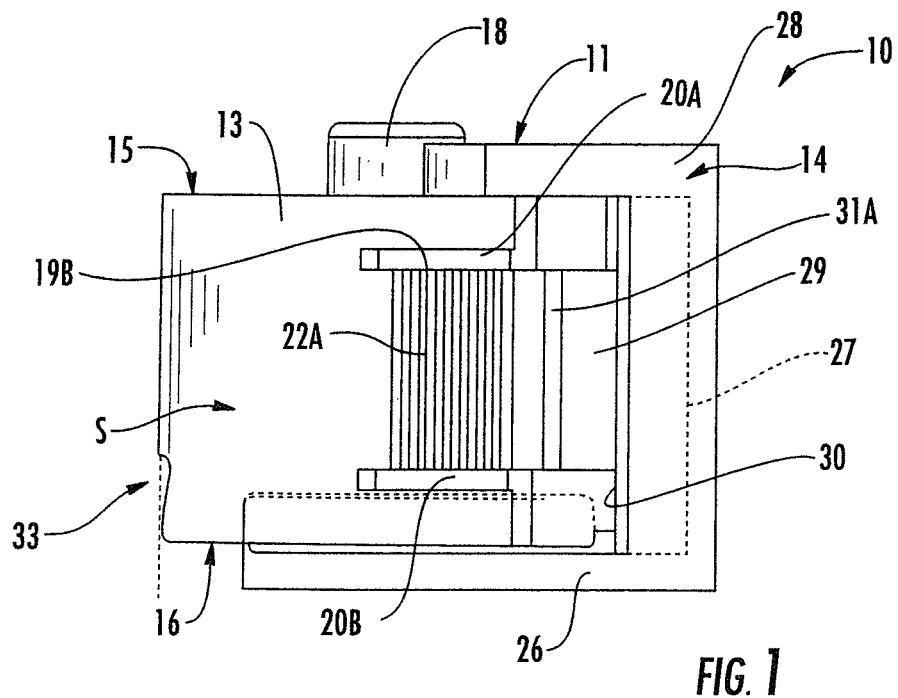
FIG. 1 is an enlarged side elevational view of the IV needle cover in open position.
Figure 2:
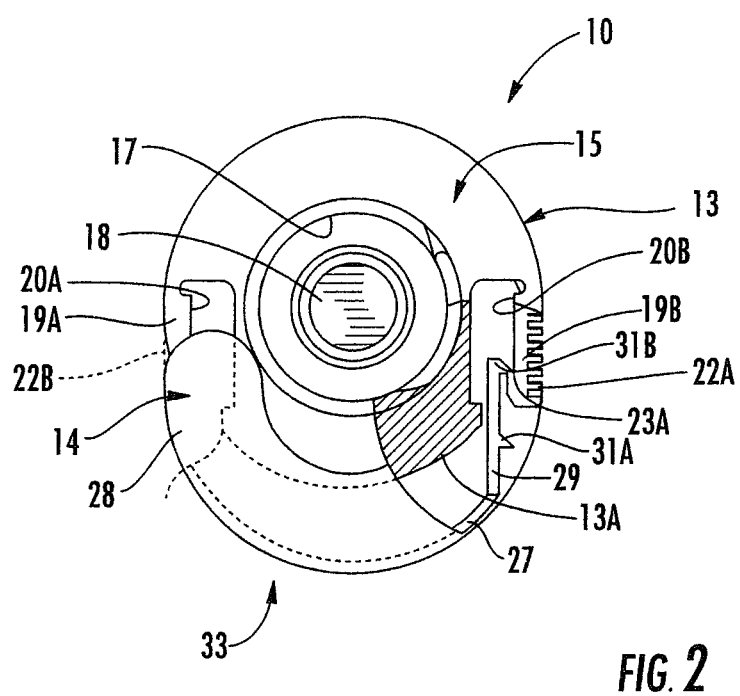
FIG. 2 is a top plan view thereof with portions broken away.
Figures 3, 4:
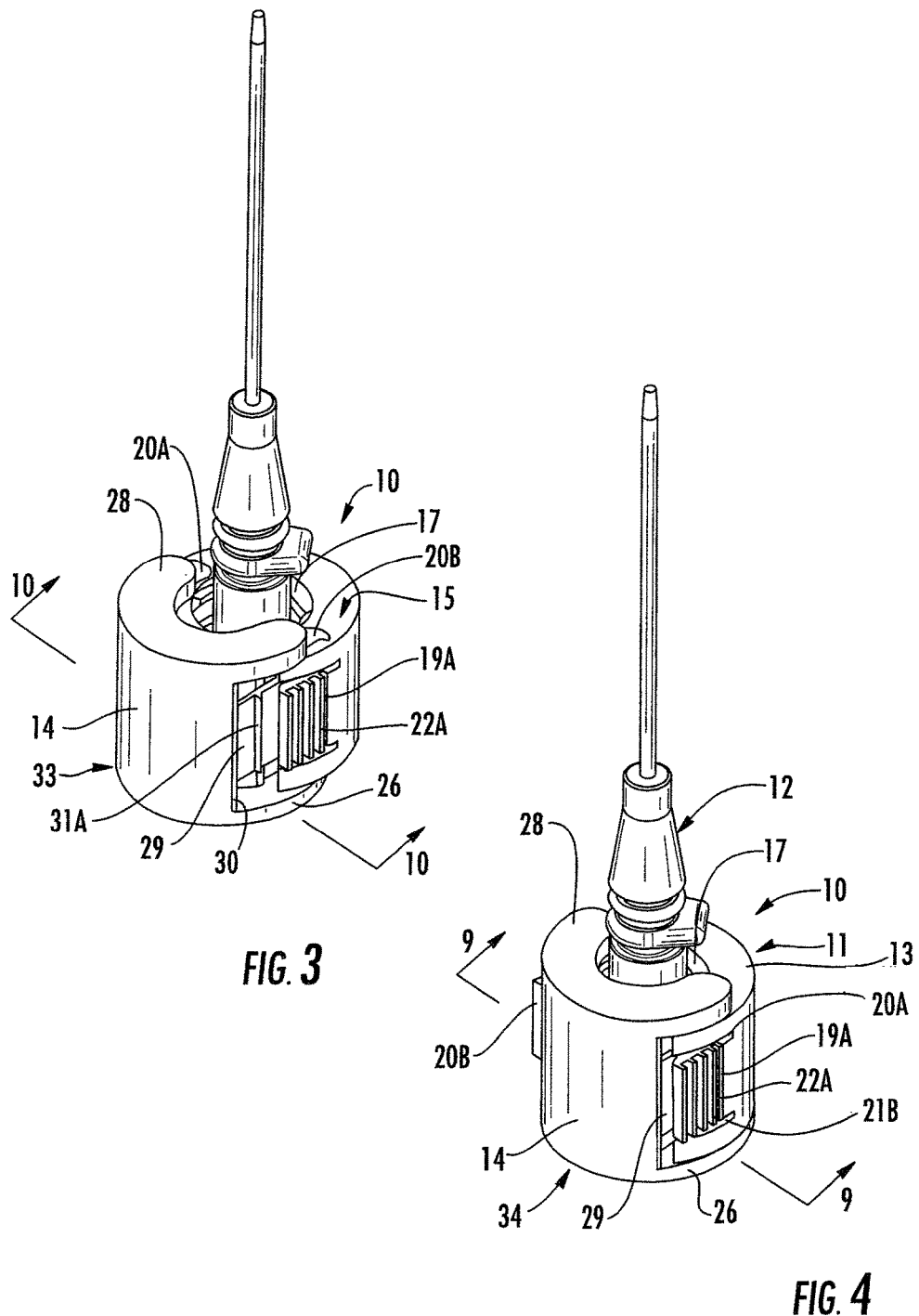
FIG. 3 is a perspective view of the IV cover in open position with an IV needle engaged therein.
FIG. 4 is a perspective view of the IV needle cover with an IV needle positioned therewithin in closed position.

Referring to FIGS. 1-3 of the drawings, an IV needle cap cover 10 of the invention can be seen having a two-part molded housing 11 selectively engaged and secured together for an IV needle 12 preventing unauthorized user access thereto as will be described in detail hereinafter.

The housing 11 has a needle receiving portion 13 and a slidably engaged needle retainment and cap clasp portion 14. The needle receiving portion 13 has a cylindrical body having a top surface 15 and a bottom surface 16 with an interiorly threaded annular bore 17 extending partially inwardly from its top surface 15 about a central upstanding needle engagement lug 18. A pair of oppositely disposed ear tabs 19A and 19B are formed in the sidewall S of the needle receiving portion 13 defined by longitudinal slots 20A and 20B therein. The needle receiving portion 13 has an area of reduced annular dimension at 13A which extends from and between the respectively defined slots 20A and 20B, best seen in cut-away view and broken lines in FIG. 2 of the drawings.

The ear tabs 19A and 19B have ribbed outer surfaces 22A and 22B and respective interior clasp retainment registration longitudinally extending edges 23A and 23B therewithin as will be described in greater detail hereinafter.

Figure 5:
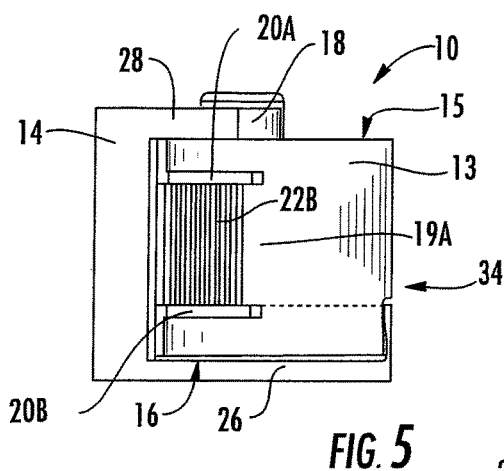
FIG. 5 is a side elevational view of the needle cover in closed position.
Figure 6:
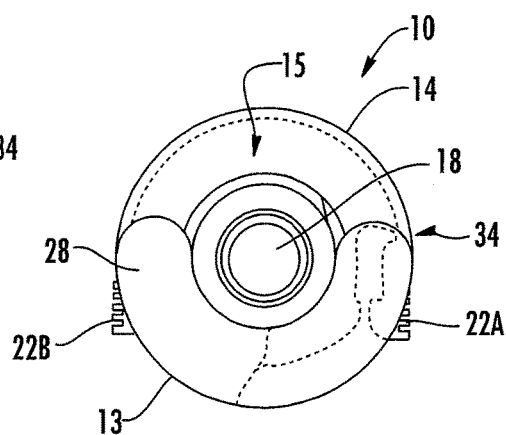
FIG. 6 is a top plan view thereof.
Figure 7:
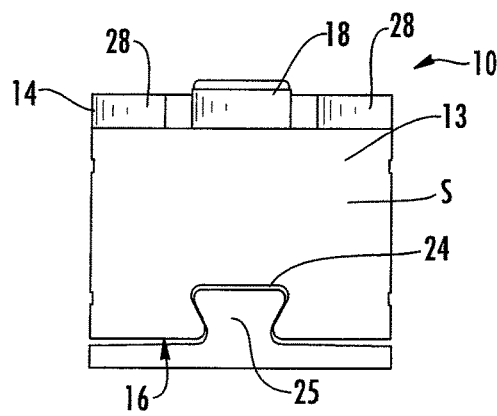
FIG. 7 is a rear elevational view thereof.
Figure 8:
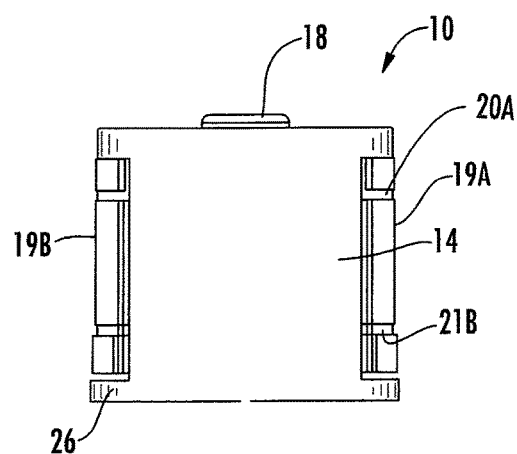
FIG. 8 is a front elevational view thereof.

Referring now to FIGS. 1, 5 and 7 of the drawings a channel 24 can be seen formed centrally across the bottom surface 16 of the cylindrical body into which a corresponding elongated registration and guide tab 25 formed on the cap clasp portion 14 can be seen having an annular base 26 with an upstanding arcuate wall 27 extending therefrom to a half arcuate upper surface portion 28 extending at right angles therefrom so as to overlie the hereinbefore described ear tab defining slots 20A and 20B as indicated in FIG. 2 of the drawings in open position and in FIG. 6 of the drawings in closed IV needle retainment position.

A pair of clasp engagement arms 29 extend from respective free edges 30 of the hereinbefore described upstanding arcuate wall 27 with spaced parallel longitudinally extending barbs 31A and 31B thereon. It will be seen that the barbs 31A and 31B selectively engage the corresponding retainment registration edges 23A and 23B providing two registration positions of the cap clasp portion 14 from an unlock access needle position as seen in FIGS. 1, 2 and 3 of the drawings to a closed barb 31A position illustrated in FIGS. 4, 5 and 6 of the drawings.

In use, the IV needle assembly 12 having a needle support and access portion 32 is threadably inserted into the threaded bore 17 over the upstanding and extending needle engagement lug 18 as best seen in FIGS. 3 and 10 of the drawings effectively blocking access to the needle fitting access portion 32. The cap clasp portion 14 is then slidably moved from a first open receiving position generally indicated at 33 in FIGS. 1, 2 and 3 of the drawings to a second tamper evident closed and locked position indicated at 34 as seen in FIGS. 4 and 9 of the drawings.

Accordingly, the respective barbs 31B lock and secure the cap clasp portion 14 preventing removal of the IV needle assembly 31.

To open, the ribbed ear tabs 19A and 19B are clasp by the user (not shown) and compressed towards one another breaking the frangible clasp engagement arms 29 releasing the cap clasp portion 14 from its closed, locked and secure position allowing it to be moved back to its first access position allowing the IV needle assembly 31 to be removed and accessed.

It will be evident that the frangible clasp engagement arms 29 assure visual indication of tampering and restrict unauthorized access by their initial locking action and can only be accessed after they are deliberately broken which requires a specific action by grasping the respective tab's outer respective ribbed surfaces 22A and 22B and compress same inwardly.

It will thus be seen that a new and novel tamper evident and resistant IV needle cap lock has been illustrated and described and it will be apparent to those skilled in the art that various changes and modifications may be made thereto without departing from the spirit of the invention.

Therefore I claim:

1. A tamper resistant and evident cap cover for engagement with an IV needle comprises, a threaded IV needle receiving portion and a retainment cap clasp portion slidably aligned together by an elongated upstanding center position registerable guide tab within a channel in a needle engagement lug of said needle receiving portion, said threaded needle receiving portion having an annular needle receiving opening within said needle engagement lug in upstanding registerable engagement within said IV needle, a tamper evident and access indicator including, a pair of oppositely disposed spaced ear tabs extending from said needle receiving portion and a pair of frangible clasp engagement arms extending from said cap clasp portion in selective registration with said ear tabs, said cap clasp portion movable from a first open receiving position to a second tamper evident closed and locked position on said needle receiving portion, said cap clasp portion having a half arcuate upper surface portion slidably disposed over a top surface portion of said IV needle receiving portion and an annular base portion in spaced vertical relation thereto, slidably positioned under said needle engagement lug of said needle receiving portion.

2. The assembly set forth in claim 1 wherein said ear tabs have textured outer gripping surfaces and a multiple spaced interior cap clasp retainment edges extending transversely from said ear tabs.

3. The assembly set forth in claim 1 wherein said frangible clasp engagement arms have elongated spaced barbs extending therefrom for select multi-positional registration with first and second retainment edges of said respective ear tabs.

* * * * *